(12) United States Patent
Reading

(10) Patent No.: US 7,578,613 B2
(45) Date of Patent: Aug. 25, 2009

(54) MODULATED DIFFERENTIAL SCANNING CALORIMETER SOLVENT LOSS CALIBRATION APPARATUS AND METHOD

(75) Inventor: Michael Reading, Leicester (GB)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 11/853,586

(22) Filed: Sep. 11, 2007

(65) Prior Publication Data

US 2008/0071494 A1    Mar. 20, 2008

Related U.S. Application Data

(60) Provisional application No. 60/844,363, filed on Sep. 14, 2006.

(51) Int. Cl.
*G01K 17/06* (2006.01)
*G01N 25/20* (2006.01)

(52) U.S. Cl. .............. 374/30; 374/11; 374/141; 422/51; 436/147

(58) Field of Classification Search .......... 374/10, 374/11, 29, 31–39, 43, 100, 30, 44, 141, 374/134, 16, 25, 27; 422/51; 436/147
See application file for complete search history.

(56) References Cited

U.S. PATENT DOCUMENTS 3,467,501 A * 9/1969 Groszek ................. 436/160
4,812,051 A * 3/1989 Paulik et al. ............ 374/10
5,224,775 A    7/1993 Reading et al.
5,255,976 A * 10/1993 Connelly ................ 374/31
5,335,993 A * 8/1994 Marcus et al. ........... 374/11
5,451,371 A * 9/1995 Zanini-Fisher et al. ... 422/51
5,967,659 A * 10/1999 Plotnikov et al. ........ 374/11
6,193,413 B1 * 2/2001 Lieberman .............. 374/45
6,535,824 B1 * 3/2003 Mansky et al. ........... 506/8
6,561,692 B2    5/2003 Danley
6,602,714 B1 * 8/2003 Tagge et al. ............. 506/37
6,869,214 B2 * 3/2005 Plotnikov et al. ........ 374/31
7,033,840 B1 * 4/2006 Tagge et al. ............. 436/147
2005/0036536 A1 * 2/2005 Lewis .................... 374/2
2005/0107959 A1 * 5/2005 Zhang ................... 702/19
2005/0141587 A1 * 6/2005 Muhlig et al. ............ 374/31

OTHER PUBLICATIONS

International Search Report dated May 12, 2008.

* cited by examiner

*Primary Examiner*—Gail Verbitsky
(74) *Attorney, Agent, or Firm*—Aslan Baghdadi; Paul, Hasting, Janofsky & Walker LLP

(57) ABSTRACT

A modulated differential scanning calorimeter that accounts for heat flow due to evaporative solvent loss. The calorimeter modulates the temperature applied to a sample and a reference to determine the amount of heat flow that is due to evaporation. By calculating the amount of heat flow due to evaporation, the user can determine how much of the heat flow of any given well is due to the process of interest as opposed to evaporation.

24 Claims, 6 Drawing Sheets

MODULATED DIFFERENTIAL SCANNING CALORIMETER SOLVENT LOSS CALIBRATION APPARATUS AND METHOD

CROSS-REFERENCE TO RELATED APPLICATION

This application claims the benefit of U.S. Provisional Patent Application Ser. No. 60/844,363 filed Sep. 14, 2006, which is herein incorporated by reference in its entirety.

BACKGROUND

1. Field of the Invention

The present invention relates to thermal analysis instruments and methods of using the same. More particularly, embodiments of the present invention relate to using modulated temperature differential scanning calorimetry to account for solvent loss during analyses conducted using open calorimeters.

2. Background of the Invention

Differential scanning calorimeters (DSCs) are used to determine physical properties of a sample by analyzing the sample's response to an applied temperature program. In operation, a DSC measures a temperature differential between a reference and a sample being analyzed in the presence of a temperature profile applied to both the reference and the sample. Using the temperature differential, certain properties of the sample being analyzed can be determined.

Two general types of temperature profiles can be used during DSC experiments. One type of temperature program is linear. The second type of temperature programs, commonly referred to as a modulate temperature program, adds a modulation to a linear temperature program. DSCs using the second type of temperature program are commonly referred to as modulated temperature DSCs. Modulated temperature DSCs are described in U.S. Pat. Nos. 5,224,775 and 6,561,692, both of which are incorporated by reference herein in their entireties.

DSC experiments can be performed using open or closed calorimeters. Open calorimeters are those that have an open sample cell. An open sample cell allows reagents to be easily added to calorimeter cells using automated pipettes. Generally, open DSCs have multiple calorimeter cells arranged in an array. In this manner, many experiments can be run in parallel. Because of the ease with which reagents can be added to calorimeter cells and the array arrangement, open calorimeters are useful in high-throughput applications.

Open DSC experiments typically involve placing a sample in a sample cell in the array, and then adding one or more reagents to the sample. For example, a number of different types of protein can be placed in an array of calorimeter cells as suspensions in water using an array of automated pipettes under robotic control. A controlled amount of ligand solution is added to each cell using automated pipettes under robotic control. By monitoring power signals from the calorimeter cells in response to an applied temperature profile, the interaction of characteristics of the various protein-ligand pairs can be rapidly assessed. This multi-sample cell architecture allows many experiments to be carried out in a rapid and efficient manner.

There is a serious disadvantage to using an open calorimeter arrangement in DSC experiments. This disadvantage is due to unknown solvent loss, which adds an uncontrolled contribution to the calorimeter measurement signal, and as a result, injects uncertainty in the calorimeter measurement.

One potential solution to this problem is to perform a differential experiment using a sample containing protein-ligand pairs, and a reference containing a same volume of solvent only, and assuming that the solvent loss in both the sample and reference cells is the same. In that way, simple subtraction could remove the unknown contribution due to solvent loss. Unfortunately, this does not solve the problem because the presence of the sample can change the rate of solvent evaporation in the sample relative to the reference. Thus, a differential arrangement with subtraction alone does not solve the problem. Further complicating the issue is that uncontrolled contribution to the heat flow caused by evaporation makes assessing enthalpies difficult because selecting the correct baseline is problematic. Similarly, when examining kinetics, the heat flow contribution from the process of interest cannot be disentangled from the heat flow contribution from solvent loss.

SUMMARY OF THE INVENTION

Embodiments of the present invention account for heat flow due to solvent loss in differential scanning calorimetry experiments. For example, differential scanning calorimeters according to embodiments of the present invention will produce a substantially better baseline from which the true thermal characteristics of the sample well may be deduced.

One embodiment of the present invention is a differential scanning calorimeter (DSC) having a sample DSC cell containing a sample comprising a solvent and a specimen to be analyzed and a reference DSC cell containing a reference solution or containing no sample. The DSC of the first embodiment also includes a first heating element for applying a modulated temperature program to the sample and reference. Further, the DSC of the first embodiment includes a first sensor for measuring a temperature of the sample and a second sensor for measuring a temperature of the reference. In addition, the first embodiment includes a computer for capturing the measured temperatures and calculating a heat capacity of the sample due to the applied modulated temperature; and to determine the amount of heat flow attributable to the evaporation of solvent from the sample DSC cell.

Another embodiment of the present invention is a differential scanning calorimeter (DSC) that includes an insulated enclosed housing unit, an array comprising a multiplicity of cells to hold one or more samples and one or more references, one or more sensors for measuring the base temperature of the sensor and the temperatures in the various cells, a heating device for exposing the samples and references to a modulated temperature program, and a computer to use a signal received from the DSC cells to calculate heat capacity independently of any kinetic process that is occurring, and to determine what portion of the received signal is due to solvent loss.

Another embodiment of the present invention is a method for accounting for solvent loss in a differential scanning calorimeter (DSC), including depositing a sample comprising a solvent and a specimen to be analyzed in a sample DSC cell, depositing solvent in a reference DSC cell, heating the sample well using a first heating element according to a modulated temperature profile, heating the reference cell using a second heating element according to the modulated temperature profile, calculating how heat flow due to solvent loss is related to changes in heat capacity as measured from the modulation from the reference cell, and using this information to calculate a baseline due to solvent evaporation from the sample DSC cell, and adjusting a DSC heat flow measurement due to the sample in accordance with the calculated baseline.

Another embodiment of the present invention is a method for accounting for evaporation loss from a solution in a sample DSC, including calibrating the DSC cell to determine the heat flow caused by solvent loss in a prior experiment using only solvent, and then subtracting from the signal from the experiment with a sample the component of heat flow due to solvent loss, where the rate of solvent loss is determined by measuring the change in heat capacity of the solution from the amplitude of the modulation, and adjusting the measured heat flow in accordance with the determined relationship between the heat flow, the solvent loss and the heat capacity as measured by the modulation.

DETAILED DESCRIPTION

Figure 1A:
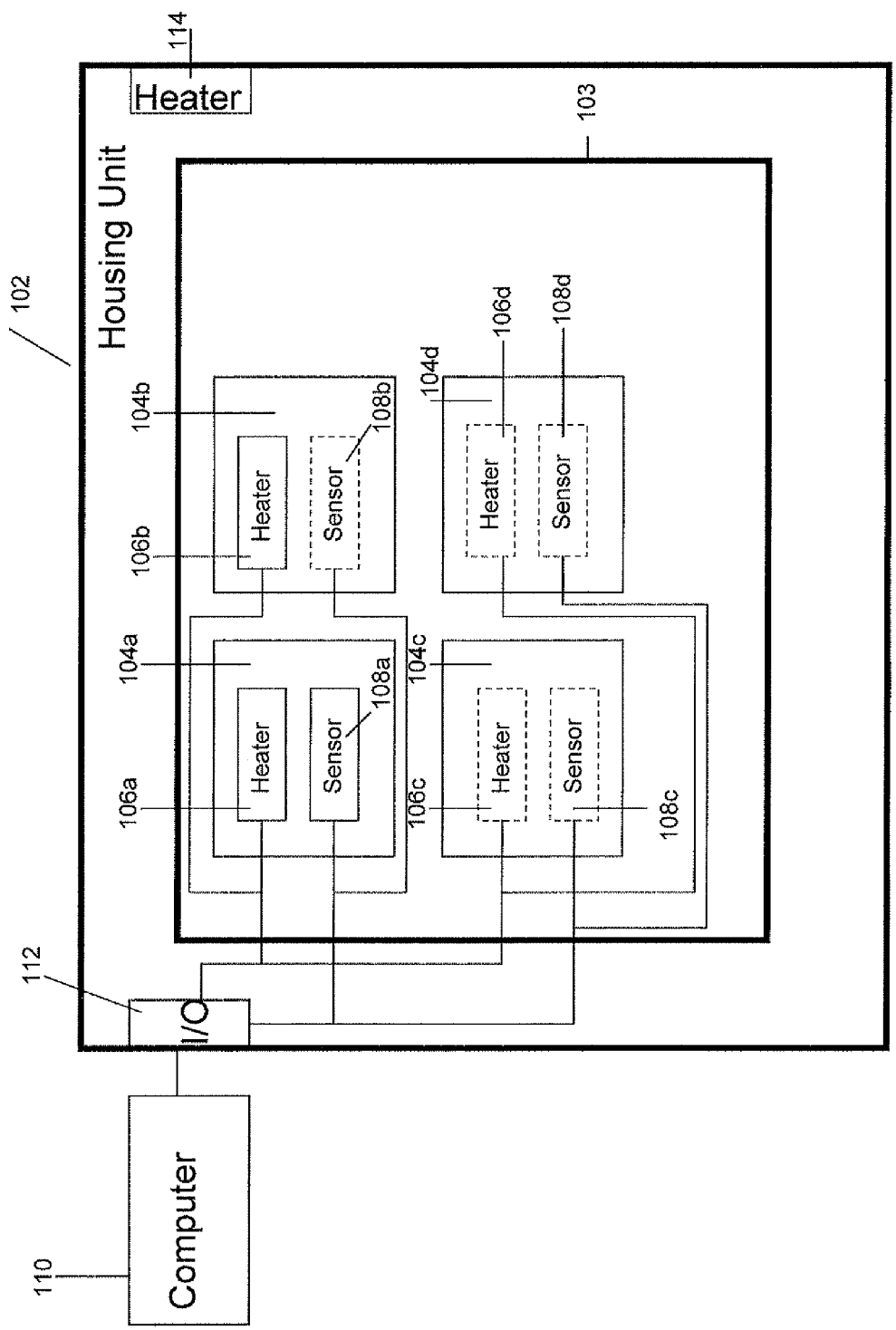
FIG. 1A is a schematic diagram illustrating a DSC according to an embodiment of the present invention.

A DSC according to one embodiment of the present invention employs temperature modulation in an open DSC to ascertain what portion of the heat flow in a given cell is due to evaporation or loss of solvent. By calculating what portion of the heat flow is due to uncontrolled solvent evaporation the part of the heat flow that derives from other processes (typically the subject of interest) can be more accurately measured. Once the amount of heat flow due to evaporation of solvent of both the reference and sample cells is accounted for, the user may then gain a more precise understanding of the heat flow due to the thermal event being measured. The terms "temperature modulation DSC," "temperature modulated DSC," "modulated DSC," and "modulation DSC" are used interchangeably herein to refer to a DSC experiment, method or apparatus that involves superimposing a periodically varying temperature perturbation during sample heat treatment, such as a linearly increasing sample temperature. Thus, a temperature modulated DSC curve may be a curve having a sinusoidal variation in temperature whose average temperature is increasing with time.

In a typical DSC, there are one or more cells, or wells, in which reagents or materials of interest can be deposited. The terms "cells" and "wells" are used interchangeably in the present specification. In an open cell DSC device, each cell is uncovered. The cells may be configured as part of a larger tray that contains many such open cells in an array. An exemplary such array is a microplate available from Vivactis of Leuven, Belgium. An open cell design allows for rapid and convenient addition of materials into the cells. For example, computers, robots, or other automated material deposition structures can deposit materials into the cells in a high throughput manner via, for example, automated pipettes. Using such automated techniques, an open DSC design array allows for a relatively high number of experiments to be run in parallel, while reducing the costs associated with multiple experiments, or the human labor required for manual deposition. In addition, the open cell design allows for greater flexibility of experimental design due to the multiplicity of possible cell configurations. Manual deposition may still be used within the spirit and scope of the present invention.

Individual cells in a DSC may be of any appropriate size, including so called "micro" or "nano" cells. In addition, the array may include any number of cells, and a single array may employ cells of varying size. In one embodiment of the present invention, each cell is capable of being heated individually by activation of any number of appropriate heating devices. For example, each cell may have its own individual heating element. These individual heating elements may be part of the array of cells, or may be part of a housing unit that houses the array of cells during the experiment. In another embodiment, there may be fewer than one heating element per cell, as each heating element may be capable of introducing a modulated temperature signal to more than one well. To ensure accurate measurements, the heating elements can be calibrated using calibration standards prior to use for analyses in a well-known manner.

FIG. 1A is a schematic diagram illustrating a DSC according to an embodiment of the present invention. Typically, a DSC according to one embodiment of the present invention includes a housing unit 102. In one embodiment of the present invention, housing unit 102 is an insulated, enclosed structure, similar to an oven, that is capable of housing a DSC cell array 103, while a temperature program is applied to one or more DSC cells. For example, in FIG. 1, DSC cells 104a, 104b, 104c, and 104d are shown. Heating can be applied to the DSC cells in a number of ways. For example, in one embodiment of the present invention, each DSC cell has a corresponding heating element that can apply heating according to a modulated temperature profile to the DSC cell. For example, as shown in FIG. 1, heating element 106a supplies heat to DSC cell 104a, heating element 106b supplies heat to DSC cell 104b, heating element 106c supplies heat to DSC cell 104c, and heating element 106d supplies heat to DSC cell 104d.

Generally, in DSC experiments the DSC cells are paired. In each pair of DSC cells, one cell is used for a reference, and the other cell is used for the sample being analyzed. For example, in FIG. 1A, DSC cell 104a may be paired with DSC cell 104b. DSC cell 104a can be used for a sample, and DSC cell 104b can be used for a corresponding reference. Similarly, DSC cell 104c may be paired with DSC cell 104d. DSC cell 104c can be used for a sample, and DSC cell 104d can be used for a corresponding reference.

Operation of the DSC is controlled using a computer 110. Computer 110 can be any well-known personal computer, microprocessor, sequencer or other computing device that can be programmed to control heaters, cause data to be captured from sensors and stored, and control automatic filling of DSC cells. Such computers are well-known.

Figure 1B:
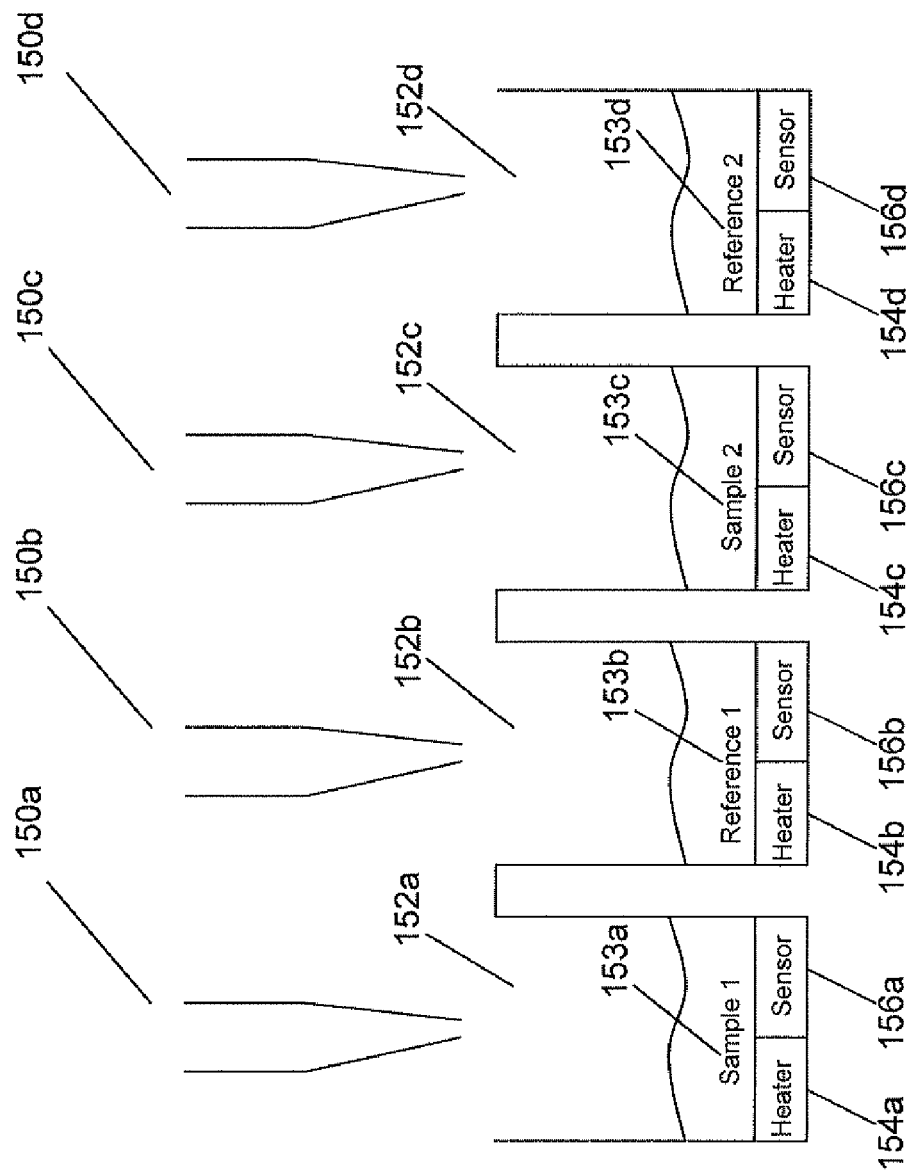
FIG. 1B is a schematic diagram illustrating automatic filling of DSC cells using pipettes.

FIG. 1B is a schematic diagram illustrating automatic filling of DSC cells using pipettes. Pipettes 150a, 150b, 150c, and 150d are used to fill respective DSC cells 152a, 152b, 152c, and 152d automatically. Pipettes 150a, 150b, 150c, and 150d are controlled by a computer, such as computer 110. In operation, the pipettes are manually or automatically (under computer control) filled with a sample or reference as desired. Under computer control, the pipettes are positioned over the DSC cell array. Computer 110 then causes the pipettes to empty their contents into the DC cells over which they are positioned.

In the example shown in FIG. 1B, the DSC cells are configured as sample reference pairs. Pipette 150a is positioned over a DSC cell 152a and fills DSC cell 152a with a sample 153a (containing, for example, solvent and protein-ligand to be studied). A heater 154a heats sample 153a according to a temperature profile under control of computer 110. A sensor 156a senses the temperature of the sample 153a and provides the sensed absolute temperature or a differential temperature (in accordance with sensor 156b) to computer 110.

A DSC cell 152b is used as the reference corresponding to the sample in DSC cell 152a. Pipette 150b is positioned over DSC cell 152b and fills DSC cell 152b with a reference 153b (containing, for example, solvent only). A heater 154b heats reference 153b according to a temperature profile under control of computer 110. A sensor 156b senses the temperature of the reference 153b and provides the sensed absolute temperature or a differential temperature (in accordance with sensor 156a) to computer 110.

Pipette 150c is positioned over a DSC cell 152c and fills DSC cell 152c with a sample 153c (containing, for example, solvent and protein-ligand to be studied). A heater 154c heats sample 153c according to a temperature profile under control of computer 110. A sensor 156c senses the temperature of the sample 153c and provides the sensed absolute temperature or a differential temperature (in accordance with sensor 156d) to computer 110.

A DSC cell 152d is used as the reference corresponding to the sample in DSC cell 152c. Pipette 150d is positioned over a DSC cell 152d and fills DSC cell 152d with a reference 153d (containing, for example, solvent only). A heater 154d heats reference 153d according to a temperature profile under control of computer 110. A sensor 156d senses the temperature of the reference 153d and provides the sensed absolute temperature or a differential temperature (in accordance with sensor 156c) to computer 110.

In another embodiment of the present invention, the housing unit has an oven that can be controlled to heat the inside of housing unit 102, for example, heater 114, according to a modulated temperature program. Such heating will cause each of the DSC elements to experience substantially the same modulated temperature program.

In another embodiment of the present invention, the housing unit can have a heating element, such as heater 114, that can provide overall heating to housing unit 102, and each of the DSC cells can have corresponding heating elements to heat their corresponding DSC cells, for example, heaters 106a, 106b, 106c, and 106d. In one such embodiment, heating element 114 is controlled by computer 110 to heat the housing unit according to a linear temperature program, and each of the DSC heating elements 106a, 106b, 106c, and 106d is controlled by computer 110 to heat their corresponding DSC cells according to an oscillating temperature program. In this manner, each of the DSC cells is effectively heated according to a modulated temperature program.

The heating elements are coupled to a computer, such as computer 110, through an input/output (I/O) port, for example I/O port 112. Computer 110 is programmed using a temperature program to control the heaters to expose samples and references to temperature profiles, such as modulated temperature profiles, as required. The heating elements can be those typically used in DSC instruments, including for example, triac heaters or resistive heaters.

The DSCs of embodiments of the present invention can be either heat-flux DSCs or power compensation DSCs. In heat flux DSCs, the temperature of the reference and sample DSC cells is measured and used to determine heat flow. The heat capacity can be derived from the measured heat flow. In power compensation DSCs, the differential power required to maintain a constant temperature of the sample and reference DSC cells is measured. The differential power is a direct measure of the heat capacity of the sample.

Each DSC cell also has a corresponding sensor. For example, as shown in FIG. 1, sensor 108a corresponds to DSC cell 104a, sensor 108b corresponds to DSC cell 104b, sensor 108c corresponds to DSC cell 104c, and sensor 108d corresponds to DSC cell 104d. The sensors can be any sensor used in typical DSC analyses, including for example, thermocouples. As is well known, some DSC heaters can perform the sensor function as well as heat the DSC according to a temperature program. Each sensor is coupled through an I/O board to computer 110. Computer 110 captures and stores the data sensed by the sensors for further analysis as described herein.

The measurements resulting from applying a modulated temperature program to the sample and reference DSC cells are used to measure heat capacities of each sample and reference independently of any kinetic process that may otherwise be occurring. The rate of change of heat capacity (i.e., the derivative of heat capacity) can be used to measure the rate of solvent loss from a DSC cell. From the enthalpy of evaporation of the solvent, the heat flow due to evaporation can be calculated from the rate of change of heat capacity.

Figure 2:
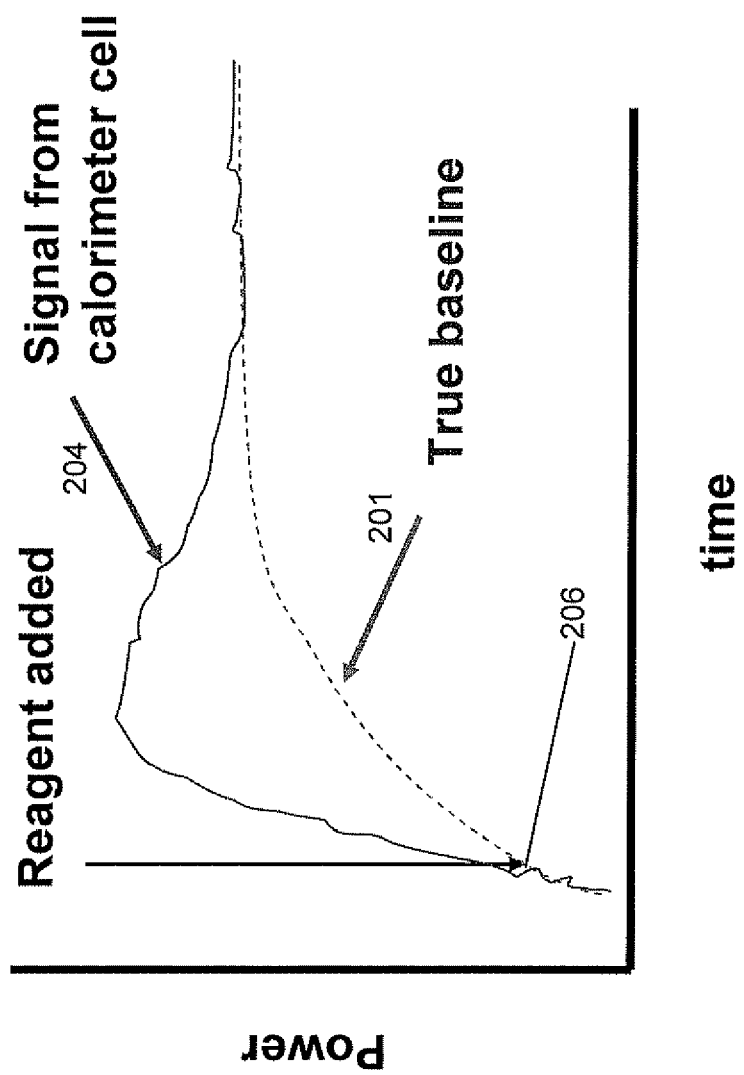
FIG. 2 is a graph illustrating an exemplary measurement curve 204 from a DSC experiment according to an embodiment of the present invention.

FIG. 2 is a graph illustrating an exemplary measurement curve 204 from a DSC experiment according to an embodiment of the present invention. Using the derivative of the heat capacity measured during a calibration run (described below), a "true baseline" curve 201 is calculated. Curve 201 represents an exemplary heat flow due to evaporation of solvent. The desired response is the difference between the measured signal and the calculated baseline (i.e., curve 204 minus curve 201). An additional piece of information, the time of the addition of reagent can also be determined as point 206 by comparing measurement curve 204 baseline curve 201.

Figure 3:
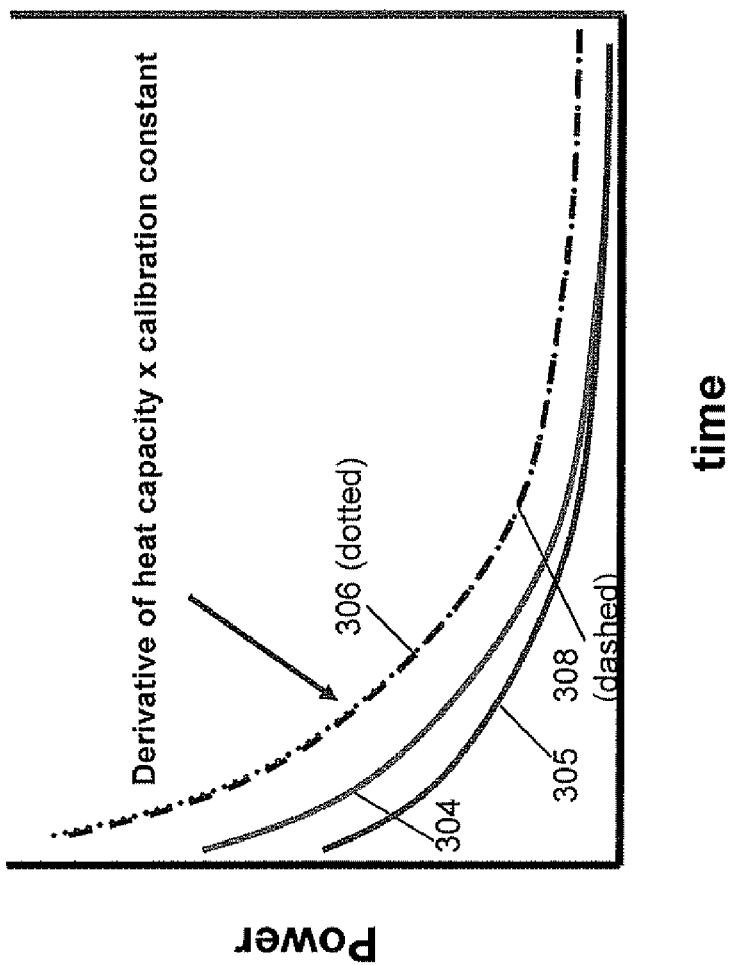
FIG. 3 is a graphical representation of several curves used in calculating a calibration constant according to one embodiment of the present invention.

"True baseline" curve 201 can be determined through a calibration procedure according to an embodiment of the present invention during which the DSC is operated using just solvent. FIG. 3 is a graphical representation of several curves used in calculating a calibration constant according to one embodiment of the present invention. Curve 304 is an exemplary heat capacity measured by applying a modulated temperature profile to a DSC cell containing only solvent. The heat capacity measured in such an experiment is a direct measure of the amount of solvent in the cell. As a result the change in heat capacity with respect to time (i.e., the derivate of the measured heat capacity) represents the rate of solvent loss (e.g., evaporation) from the DC cell. Curve 305 is the derivative of measured heat capacity curve 304 according to an embodiment of the present invention. This curve is the same as the power curve 306 (dotted) due to solvent loss multiplied by some constant. As a result, when multiplied by an appropriate calibration constant, the derivative of heat capacity (i.e., the rate of solvent loss) overlays the power curve due to solvent loss. This product (derivative of heat capacity times a calibration constant) is illustrated by curve 308 (dashed), which overlays the power curve due to solvent loss, curve 306. The power curve due to solvent loss is the total signal in an isothermal experiment or the non-reversing heat flow in a scanning experiment.

Figure 4:
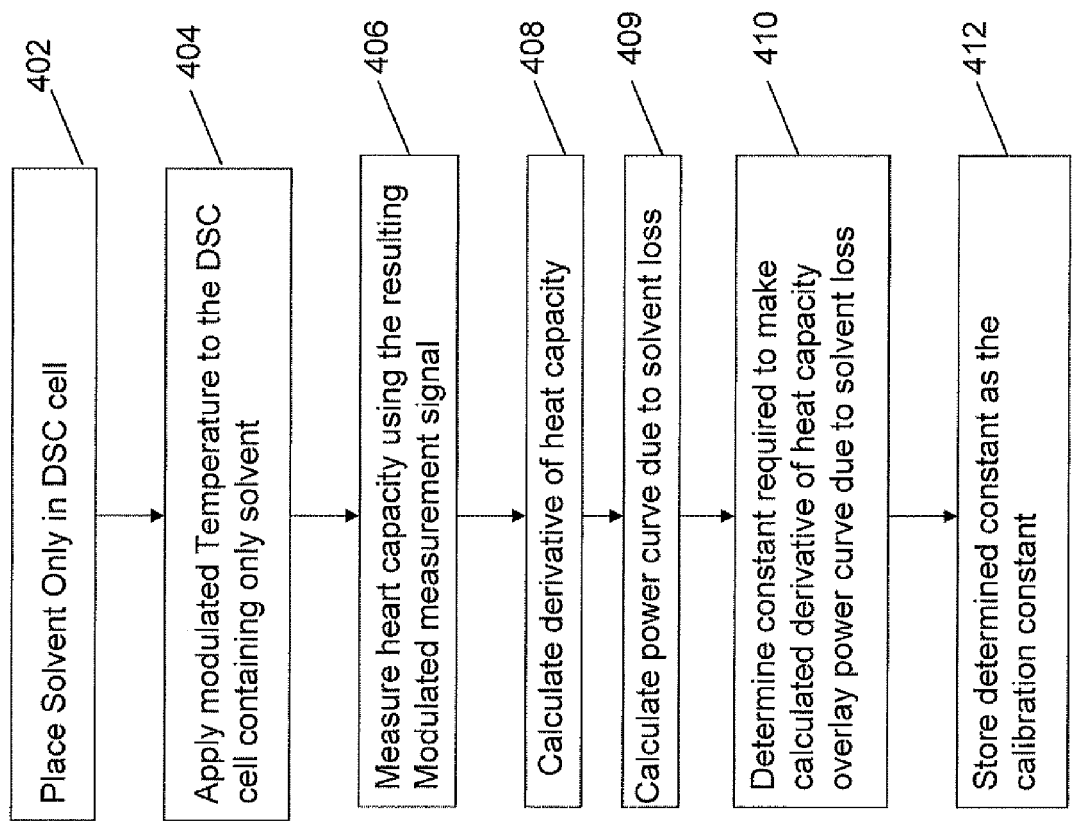
FIG. 4 is a flow chart that depicts exemplary steps involved in a method for determining a calibration constant, according to an embodiment of the present invention.

FIG. 4 is a flow chart for determining the calibration constant according to an embodiment of the present invention. In step 402, a DSC cell is filled with solvent only. In step 404, a modulated temperature program is applied to the DSC cell containing solvent only and a measurement signal collected. In step 406, the heat capacity is determined from the measurement signal. In a modulation DSC experiment, the measurement signal can be deconvoluted to produce reversing heat capacity, among other quantities.

In step 408, the derivative of the reversing heat capacity is calculated.

In step 409, the curve representing the power due to solvent loss is calculated. The power due to solvent loss is the total signal in an isothermal experiment or the non-reversing heat flow in a scanning experiment. The non-reversing heat flow is also obtainable by measuring the heat flow signal of the solvent in a modulation DSC experiment and deconvoluting the signal.

In step 410, the constant required to cause the calculated derivative of heat capacity to overlay the power due to solvent loss curve is calculated. This can be done by any of a number of curve fitting techniques.

In step 412, the determined constant is stored as the calibration constant.

In another embodiment of the invention, the steps illustrated in FIG. 4 may be carried out using temperature modulation DSC performed on a solvent in the presence of one or more other materials. However, such a system must produce no other processes during the thermal treatment other than evaporation of the solvent. Accordingly, it is preferable that the method of FIG. 4 be carried out as indicated in step 402, in which solvent only is used in the DSC cell.

The calibration constant determined according to the method outlined in FIG. 4 is used to calculate a "true baseline" as shown in FIG. 2.

Figure 5:
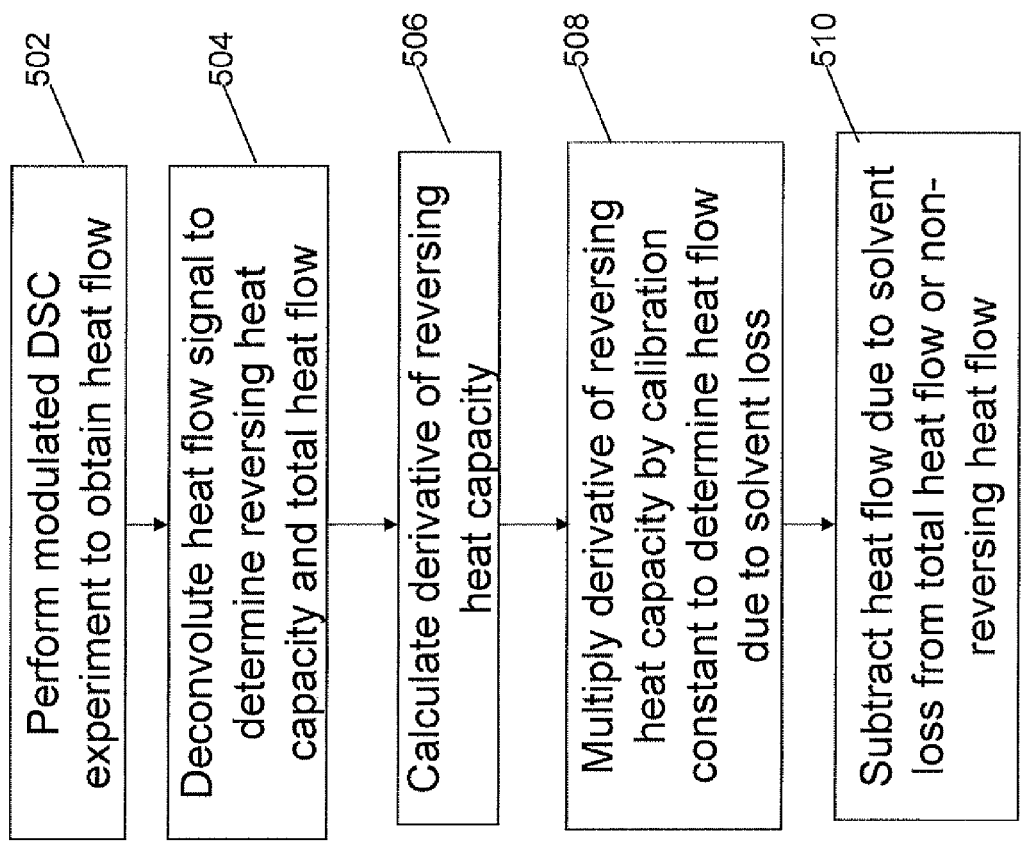
FIG. 5 is a flow chart that depicts exemplary steps involved in a method for calculating the true baseline for a sample measurement in which solvent loss takes place, according to an embodiment of the present invention.

FIG. 5 is a flow chart that depicts exemplary steps involved in a method for accounting for solvent loss in a DSC experiment, according to an embodiment of the present invention.

In step 502, a DSC experiment is performed by applying a modulated temperature to a sample disposed in solvent to obtain a heat flow signal. In step 504, the heat flow signal is deconvoluted to calculate a reversing heat capacity, as well as the total heat flow. In step 506, the derivative of the reversing heat capacity is calculated. In step 508, the calculated derivative of the reversing heat capacity is multiplied by the calibration constant calculated in step 410 to derive the heat flow due to solvent loss, which can be used as a true baseline for subtraction from experimental DCS curves. In step 510, the derived heat flow due to solvent loss is subtracted from the curves representing total or non-reversing heat flow (which can also be determined from the deconvolution of step 504), as appropriate.

In summary, in accordance with embodiments of the present invention, a calibration constant obtained during heating of a pure solvent can be used together with a heat capacity measurement from a temperature modulation DSC experiment of a sample disposed in the solvent, in order to calculate the "true baseline" as shown, for example, in FIG. 2. During an analysis run, the "true baseline" is subtracted from the total (for isothermal experiments) or non-reversing (for scanning or non-isothermal experiments) heat flow as appropriate, in order to determine the heat flow due to the thermal event being analyzed.

The modulated temperature caused by the individual heating element can be of any appropriate type. For example, the modulation a square wave, a sine wave, a triangle wave, a sawtooth wave, any combination of these in a periodic or random manner, or any other appropriate modulated signal. The modulation can be periodic or aperiodic.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A differential scanning calorimeter (DSC), comprising:
   a sample DSC cell containing a sample comprising a solvent and a specimen to be analyzed;
   a reference DSC cell containing a reference solution;
   a first heating element for applying a modulated temperature program to the sample;
   a second heating element for applying a modulated temperature program to the reference;
   a first sensor for measuring a temperature of the sample;
   a second sensor for measuring a temperature of the reference; and
   a computer for capturing the measured temperatures and calculating a heat capacity of the sample from the applied modulated temperature; and to determine the amount of heat flow attributable to the evaporation of solvent from the sample DSC cell.

2. The differential scanning calorimeter of claim 1, wherein the differential scanning calorimeter is a heat-flux DSC.

3. The differential scanning calorimeter of the claim 1, wherein the differential scanning calorimeter is a power compensation DSC.

4. The differential scanning calorimeter of claim 1, wherein the first and second heating elements modulate temperature according to one of a sine wave, a square wave, a sawtooth wave, a triangle wave or any combination of these in a periodic or random manner.

5. The differential scanning calorimeter of claim 1, wherein the DSC is calibrated using a DSC cell containing solvent only to determine the parameters necessary to provide a baseline due to solvent evaporation.

6. The differential scanning calorimeter of claim 5, wherein the baseline is subtracted from a measured heat flow.

7. The differential scanning calorimeter of claim 1, wherein the DSC comprises an array of DSC cells.

8. A method for accounting for solvent loss in a differential scanning calorimeter (DSC), comprising:
   depositing a sample comprising a solvent and a specimen to be analyzed in a sample DSC cell;
   depositing a reference in a reference DSC cell;

heating the sample cell using a first heating element according to a modulated temperature profile;

heating the reference cell using a second heating element according to the modulated temperature profile;

calculating a baseline representing heat flow due to solvent evaporation from the sample DSC cell; and adjusting a DSC heat flow measurement due to the sample in accordance with the calculated baseline.

9. The method recited in claim 8, comprising calibrating the DSC to determine the baseline.

10. The method recited in claim 9, further comprising operating the DSC with a DSC cell containing only solvent.

11. The method recited in claim 8, wherein the temperature is modulated according to one of a sine wave, a square wave, a sawtooth wave, and a triangle wave in a periodic or random manner.

12. The method recited in claim 8, wherein the adjusting the DSC heat flow measurement step comprises subtracting the calculated baseline due to solvent loss from the DSC heat flow measurement.

13. The method recited in claim 8, comprising using an array of DSC cells.

14. The method recited in claim 13, comprising using an array of paired DSC cells, wherein one cell of the pair is for a sample, and the other DSC cell of the pair is for a reference.

15. A differential scanning calorimeter (DSC) that accounts for heat flow due to solvent loss from a cell, comprising:

an insulated enclosed housing unit;

an array consisting of a multiplicity of cells to hold one or more samples and one or more references;

one or more sensors for measuring a reference temperature and a sample temperature in one or more cells of the multiplicity of cells;

a heating device for exposing the samples and references to a modulated temperature program; and a computer to use a signal received from one or more cells of the multiplicity of cells to calculate heat capacity of a sample in the one or more cells independently of any kinetic process that is occurring and to determine from the received signal an amount of heat flow that is due to solvent loss from the one or more cells.

16. The DSC of claim 15, wherein each cell can be heated simultaneously by one or more heat sources.

17. The DSC of claim 15, wherein each cell can be heated independently by one or more heat sources.

18. The DSC of claim 15, wherein the cell array can be loaded using automated means.

19. The DSC of claim 15, wherein the cell array can be loaded using manual means.

20. The DSC of claim 15, wherein the cell array allows for varying cell sizes.

21. The DSC of claim 15, wherein there is a heating device used to regulate the temperature within the housing unit.

22. The DSC of claim 15, wherein output of the device is automatically fed into a computing device that automatically calculates and records measurements.

23. A method for determining in a DSC thermal characteristics of a sample disposed in a solvent, comprising:

performing a modulated DSC measurement upon the sample disposed in the solvent to obtain an experimental sample heat flow curve, wherein the performing the modulated DSC measurement comprises superimposing a periodically varying temperature perturbation on a linearly increasing sample temperature during sample heat treatment;

deconvoluting the experimental sample heat flow curve to obtain a reversing heat capacity curve, a non-reversing heat flow curve and a total heat flow curve;

calculating a derivative of the reversing heat capacity curve based on the modulated DSC measurement of the sample;

multiplying the derivative of reversing heat capacity curve by a calibration constant to obtain a true baseline representing heat flow due to solvent loss when the sample is disposed in the solvent, wherein the calibration constant, when applied to a derivative heat capacity curve of the solvent, causes the derivative heat capacity curve of the solvent to overlay a power curve due to solvent loss; and subtracting the true baseline from at least one of the non-reversing heat flow and the total heat flow.

24. The method of claim 23, wherein the derivative heat capacity curve of the solvent is determined by:

performing a modulated DSC measurement upon a solvent disposed in a DSC cell;

determining a heat capacity curve for the solvent using a modulated measurement signal derived from the modulated DSC measurement; and calculating the derivative heat capacity curve from the heat capacity curve.

* * * * *